United States Patent [19]

Mengler et al.

[11] 3,951,965

[45] Apr. 20, 1976

[54] BIS-TRIAZINYL-AMINO)-STILBENE-DISULFONIC ACID DERIVATIVES

[75] Inventors: Helmut Mengler, Frankfurt am Main; Erich Schinzel, Hofheim, Taunus; Günter Rösch, Altenhain, Taunus, all of Germany

[73] Assignee: Hoechst Aktiengesellschaft, Frankfurt am Main, Germany

[22] Filed: Sept. 18, 1974

[21] Appl. No.: 506,985

[30] Foreign Application Priority Data

Sept. 21, 1973 Switzerland.................... 13558/73

[52] U.S. Cl. .................. 260/240 B; 252/301.23; 260/248 NS; 427/64
[51] Int. Cl.².................................. C07D 403/10
[58] Field of Search ................. 260/240 B, 248 NS

[56] References Cited

UNITED STATES PATENTS

| | | | |
|---|---|---|---|
| 2,840,557 | 6/1958 | Williams et al. ................ | 260/240 B |
| 3,600,385 | 8/1971 | Loffelman et al. ............. | 260/240 B |
| 3,663,538 | 5/1972 | Lebkücher et al. ............. | 260/240 B |
| 3,757,010 | 9/1973 | Balzer et al. .................... | 260/240 B |

*Primary Examiner*—Arthur P. Demers
*Attorney, Agent, or Firm*—Connolly and Hutz

[57] ABSTRACT

Condensation compounds of 2 mols of cyanuric acid with 1 mol of 4,4'-diaminostilbene-2,2'-disulfonic acid, at least two mols of a lower alkylene diamine which is acylated at one nitrogen atom and, optionally, another two mols of another amine or an alcohol or a phenol are useful as optical brighteners, especially for cellulosic and polyamide materials.

12 Claims, No Drawings

BIS-TRIAZINYL-AMINO)-STILBENE-DISULFONIC ACID DERIVATIVES

Optical brighteners of the 4,4'-bis-(triazinylamino)-stilbene-2,2'-disulfonic acid series are known for a long time.

It has now been found that the novel compounds of the formula I

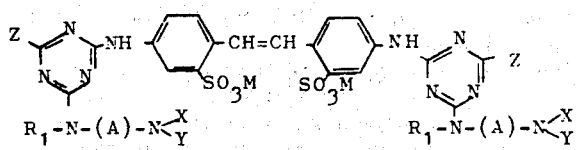

where

X is $-CO-R_2$, $-SO_2R_3$, $-CO-O-R_3$, $-CO-NH-R_2$ or $-CS-NH-R_2$;

Y is $-CO-R_3$ or $R_4$, or, when X stands for $-CO-R_2$, $R_2$ and Y together form a chain having from 3 to 5 carbon atoms which is composed of the following members in any sequence whatsoever;
  *a* methylene groups, *b* ethenylene groups, *c* ortho-phenylene groups, and *d* carbonyl groups, *a* being from zero to 5, *b* from zero to 2 and *c* and *d* are zero or 1 and *a* being greater than 3 in the case where *b*, *c* and *d* are zero;

$R_1$, $R_2$ and $R_4$, independently, each are a hydrogen atom, an alkyl radical having up to 20 carbon atoms, a cycloalkyl radical having from 4 to 8 carbon atoms or a phenyl radical;

$R_3$ is an alkyl radical having up to 20 carbon atoms, a cycloalkyl radical having from 4 to 8 carbon atoms or a phenyl radical;

A is an alkylene group having from 2 to 6 carbon atoms; and

Z is a chlorine atom or a group of the formula II

or $O-R_7$,
where $R_5$ is a hydrogen atom, an alkyl or alkenyl radical having up to 20 carbon atoms, a cycloalkyl radical having from 4 to 8 carbon atoms, or a phenyl radical;

$R_6$ is a hydrogen atom or a lower alkyl radical; or $R_5$ and $R_6$, together with the nitrogen atom, stand for a hydrogenated 5- or 6-membered ring;

$R_7$ is a lower alkyl or phenyl radical; and

M is a hydrogen atom or a colorless cation; and wherein the radicals $R_1$ to $R_7$ may be substituted by non-chromophoric radicals, are valuable optical brighteners for textile and non-textile materials.

Preferred compounds of formula I are those where $R_1$ is a hydrogen atom, a lower alkyl group being optionally substituted by a hydroxy or a lower alkoxy group or a group of the formula —NXY, wherein X and Y are defined as follows; a benzyl group or cyclohexyl group;

X is $-CO-R_2$, $-CO-NH-R_2$, $-SO_2-R_3$ or $-CO-O-R_3$, wherein $R_2$ is a hydrogen atom, an alkyl group having up to 18 carbon atoms, a lower alkyl group being substituted by a hydroxy, carboxy, sulfo or phenyl group, the cyclohexyl group or a phenyl group optionally substituted by chlorine atoms, lower alkyl or lower alkoxy groups, and $R_3$ is a lower alkyl, benzyl, phenyl or tolyl group;

Y is a hydrogen atom, a lower alkyl group, a cyclohexyl or phenyl group or, when X is $CO-R_2$, $R_2$ and Y together are an alkylene group having 4 or 5 carbon atoms, an alkylene-oxo group having from 2 to 4 carbon atoms in the alkylene radical, an ethenylene-oxo, ortho-phenylene-oxo or butadienylene group;

A is an alkylene group having from 2 to 6 carbon atoms;

Z is a chlorine atom or a group of the formula $-NR_5R_6$ or $-OR_7$, where $R_5$ is a hydrogen atom, a lower alkyl group which may be substituted by a hydroxy, lower alkoxy, carboxy, sulfo or phenyl group;
  a lower alkenyl group, the cyclohexyl group or a phenyl group optionally substituted by chlorine atoms, lower alkyl, lower alkoxy, carboxy or sulfo groups, or a group of the formula $-A-NXY$, where A, X and Y are as defined above, $R_6$ is a hydrogen atom, a lower alkyl group optionally substituted by a hydroxy, carboxy, sulfo or a lower alkoxy group, or $R_5$ and $R_6$ together with the nitrogen atom are a pyrrolidine, piperidine, hexamethylene-imine or morpholine radical, $R_7$ is a lower alkyl group, a lower alkyl chain optionally interrupted by an oxygen atom, or a phenyl radical, and M is a hydrogen atom, an alkali metal cation, an equivalent of an alkaline earth metal cation or an ammonium ion.

Especially interesting are compounds of the formula I,
where

A is an alkylene radical having from 2 to 6 carbon atoms, $R_1$ is a hydrogen atom, a lower alkyl group or a group of the formula $-A-NXY$, where A is as defined above and X and Y are as defined as follows, X is $-CO-R'_2$, $-CO-NH-R''_2$, $-SO_2-R'_3$ or $-CO-O-R''_3$, where $R'_2$ is a hydrogen atom, an alkyl radical having up to 18 carbon atoms, a lower carboxyalkyl radical or a phenyl radical, $R''_2$ is a hydrogen atom, a lower alkyl or phenyl radical, $R'_3$ is a phenyl or tolyl radical and $R''_3$ is a lower alkyl or phenyl radical, Y is a hydrogen atom or, when $R'_2$ is a lower alkyl radical, also a lower alkyl, a cyclohexyl or phenyl radical, or Y and $R'_2$ together are an alkylene group having 4 or 5 carbon atoms, an ethylene-oxo, ethenylene-oxo, ortho-phenylene-oxo or butadienylene group, Z is a chlorine atom or a group of the formula $-NR_5R_6$ or $-OR_7$, where $R_5$ is an alkyl radical having up to 18 carbon atoms, a lower alkyl radical which may be substituted by hydroxy, carboxy or sulfo groups, a lower alkenyl radical, a phenyl radical being optionally substituted by sulfo groups, or a group of the formula $-A-NXY$, where A, X and Y are as defined above, $R_6$ is a hydrogen atom or a lower alkyl radical being optionally substituted by a hydroxy group, or $R_5$ and $R_6$ together with the nitrogen atom form a pyrrolidine, piperidine or morpholine radical, and $R_7$ is a lower alkyl radical being optionally substituted by a lower alkoxy group, or a phenyl radical, and M is a hydrogen or alkali metal ion or an ammonium ion of the formula $NH_xR_{4-x}$, where R represents identical or different lower alkoxy groups optionally substituted by a hydroxy group, and x stands for a number of from 1 to 4.

By "lower" or "low molecular weight" in connection with aliphatic radicals there are to be understood those radicals having up to 6, especially up to 4 carbon atoms.

By "non-chromophoric" or "non-color-effecting" substituents there are to be understood those which shown none or insignificant adsorption in the visible range, especially preferably lower, alkyl, alkenyl or alkoxy radicals, acyl radicals, halogen atoms, preferably chlorine or bromine atoms, amino, lower mono- or dialkylamino radicals and the trialkylammonium groups deriving therefrom with colorless anions, optionally acylated hydroxy or amino groups, optionally functionally modified carboxy or sulfo radicals, and aryl radicals, especially phenyl radicals. Of course, the cited radicals may be substituted again by non-chromophoric radicals such as lower alkyl radicals by halogen atoms, hydroxy or the cited amino radicals, optionally functionally modified carboxy groups or phenyl groups, or phenyl radicals carrying one or more substituents such as lower alkyl or alkoxy groups, acyl radicals, halogen atoms or optionally functionally modified carboxy or sulfo groups.

When a hydroxy group or amino group may be "esterified" or "acylated", or "acyl radicals" are mentioned, there is to be understood above all an acyl radical deriving from a low molecular weight aliphatic carboxylic acid or an optionally substituted benzoic acid, especially lower alkanoyl radicals and the benzoyl radical.

By "functionally modified" carboxy groups there are to be understood especially the salts thereof with colorless cations, esters with non-chromophoric alcohol radicals, amides, the nitrogen atom of which may carry one or two non-chromophoric radicals, or the cyano group.

Among the esters, lower alkyl esters are preferred the alkyl group of which may be substituted by hydroxy or lower dialkylamino groups.

The above indications with respect to salts, esters and amides are correspondingly valid also for "functionally modified" sulfo groups.

The compounds of the formula I in accordance with the present invention may be prepared by condensing 2 mols of an amine of the formula III

in aqueous solvents or in water alone, optionally in the presence of acid binding agents, with 2 mols of cyanuric acid chloride, 1 mol of 4,4'-diaminostilbene-2,2'-disulfonic acid and 2 mols of an amine or alcohol or phenol of the formula ZH under usual conditions in several steps. The sequence of the condensation steps depends on the reactivity of the corresponding reactants. It is also possible to condense 4 mols of an amine of the formula III with 2 mols of cyanuric acid chloride and 1 mol of 4,4'-diaminostilbene-2,2'-disulfonic acid. In the case where Z is Cl, the amine of formula III is introduced in the second reaction step, and the third chlorine atom is maintained in the molecule.

The compounds of formula I are isolated in known manner in the form of salts or free acids. By reaction of the free acids with suitable amines, for example, ammonium salts being easily soluble in polar solvents, especially easily soluble in water are obtained.

In formula I, Z may stand for the following suitable radicals of amines:

orthanilic acid, chloroaniline-sulfonic acids, chloroanilinedisulfonic acids, amides of the cited and following anilinesulfonic acids carrying different substituents at the benzene nucleus, dichloroanilines, 4,5-dichloroaniline-2-sulfonic acid, toluidines, toluidine-sulfonic acids, toluidine-disulfonic acids, chlorotoluidines, chlorotoluidine-sulfonic acids, 1-amino-2-methyl-3-chlorobenzene-4,6-disulfonic acid, anisidines, 6-chloro-4-amino-1-methoxybenzene-3-sulfonic acid, phenetidines, N-methyltoluidines, N-methylanisidines, N-methylphenetidines, aminobenzoic acids, lower aminobenzoic acid alkyl esters, aminobenzoic acid amides, aminophthalic acids, lower aminophthalic acid alkyl esters, N-methylbenzylamine, pyrrolidine, piperidine, hydroxypiperidine, hexamethyleneimine, 2-methyl-morpholine, 2,6-dimethyl-morpholine, thiomorpholine, 3-aminopropionitrile, 2-($\beta$-hydroxy-ethoxy)ethylamine, n- or iso-propylamine, propanolamine, 2-propanolamine, 3-methoxypropylamine, n-butylamine, n-hexylamine, cyclohexylamine, stearylamine, allylamine, oleylamine, N-ethylglycine, diethylamine-2,2'-disulfonic acid, iminodiacetic acid, di-n-propylamine, di-isopropylamine, di-(2-propanol)-amine, N-n-butyl-ethanolamine or di-n-butylamine.

Furthermore, Z may be the radical of a phenol optionally substituted by non-color-effecting groups or groups which do not interfere with the fluorescence, or the radical of an alcohol such as propanol, isopropanol, n-butanol, ethylene-glycol, ethylene-glycol-mono-n-butyl ether or diglycol(ethyleneglycol-mono-$\beta$-hydroxyethyl ether).

Especially interesting are compounds of formula I where Z stands for the radicals of the following amines or alcohols: aniline, metanilic acid, sulfanilic acid, aniline-2,4-disulfonic acid, aniline-2,5-disulfonic acid, aniline-3,5-disulfonic acid, chloroanilines, N-methylaniline, aminobenzonitriles, benzylamine, morpholine, methylamine, ethylamine, ethanolamine, taurine, glycine, dimethylamine, diethylamine, diethanolamine, N-methylethanolamine, N-methyltaurine, sarkosine, methanol, ethanol, methylglycol (ethyleneglycol monomethyl ether) or lower diglycol mono-alkyl ethers.

M stands for example for:
the hydrogen ion, an alkali metal cation, an ammonium ion deriving from ammonia or a nitrogen containing organic compound of basic character, furthermore an equivalent of an alkaline earth metal or aluminum cation. Suitable basic nitrogen containing organic compounds are for example: guanidine, S-alkyl, or S-aryl-isothio-ureas, for example S-benzyl-isothio-urea, aromatic amines, for example aniline or p-toluidine, especially, however, primary, secondary or tertiary aliphatic amines, for example triethylamine, ethanolamine, diethanolamine, triethanolamine or morpholine. The salts of these amines are suitable above all for the preparation of high percentage liquid formulations of the compounds of the invention in solvents, above all polar solvents, especially water.

The amines of formula III are known. Preferably, those amines of formula III are used wherein A is propylene. These amines of the formula III or IV

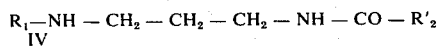
IV are obtained according to known methods by addition of carboxylic acid or sulfonic acid amides, imides or lactams on acrylonitrile or, optionally, by addition of ammonia or suitable primary amines onto acrylonitrile, and subsequent acylation at the nitrogen atom of the terminal amino group. Subsequently, the nitrile group is catalytically hydrogenated, optionally in the presence of an amine of the formula $R_1NH_2$.

Suitable carboxylic acid or sulfonic acid amides or acid amide-like compounds for the known addition onto acrylonitrile are, for example, the following compounds:
formamide, N-methylformamide, N-n- and iso-propyl-formamide, N-n- and iso-butylformamide, N-n-hexyl-formamide, N-isohexylformamide, N-cyclohexylformamide, formanilide, acetamide, N-methylacetamide, acetanilide, propionamide, N-methylpropionamide, butyric acid amide, the amides of the higher fatty acids such as palmitic acid amide or stearic acid amide, phenylacetic acid amide, benzamide, N-methylbenzamide, benzanilide, ε-caprolactam, 2-hydroxypyridine, carboxylic acid imides such as succinimide or phthalimide, aliphatic sulfonamides such as methanesulfonamide, ethanesulfonamide, n-propanesulfonamide, propane-sulfone-N-methylamide, n-butanesulfonamide or benzylsulfonamide, aromatic sulfonamides such as benzenesulfonamide, benzensulfone-N-methylamide or toluene-sulfonamides, urea, substituted ureas such as methyl-, ethyl- or phenyl-urea, urethanes such as N-methyl-, N-ethyl- or N-phenyl-urethane, thio-urea or substituted thio-ureas such as methyl- or phenylthio-urea.

When di-adducts are formed, for example with benzenesulfonamide or p-toluene-sulfonamide, the mono-adduct may be easily obtained by treatment with alkali, while 1 mol of acrylonitrile is separated.

Suitable amines of the formula $R_1-NH_2$, in the presence of which the catalytic hydrogenation of the nitriles may be carried out, are especially the following ones: methylamine, ethylamine, propylamine, butylamine, hydroxy-ethylamine, β-hydroxypropylamine, benzylamine, cyclohexylamine or aniline.

Furthermore, there may be used the following compounds as amines of formula III:
N-formyl-ethylene-diamine, N-acetyl-ethylene-diamine, N-n-butyl-N-acetyl-ethylene-diamine, N,N'-di-n-butyl-N-formylethylene-diamine, N,N'-di-n-butyl-N-acetyl-ethylene-diamine, N,N'-di-dodecyl-N-acetyl-ethylene-diamine, N-propionyl-ethylenediamine, N-n-butyryl-ethylene-diamine, N-isobutyryl-ethylenediamine, N-isovaleroyl-ethylene-diamine, N-n-caproyl-ethylenediamine, N-diethylacetyl-ethylene-diamine, N-carbamoyltetramethylene-diamine, N-(2-aminoethyl)-benzene-sulfonamide or N-(6-amino-n-hexyl)-benzene-sulfonamide.

The compounds of formula I in accordance with the present invention are optical brighteners for materials of natural cellulose such as cotton, paper and finely distributed wood masses, or for materials of regenerated cellulose, wool or synthetic polymides and polyurethane. The organic materials to be brightened optically may be present in their different stages of processing (raw material, semi-finished goods or finished articles) and in their various forms of end products (fibers, filaments, knitted or woven fabrics, fleeces, sheets and the like).

However, fibers, filaments, textiles, fleeces, sheets or paper of natural or regenerated cellulose and fibers, filaments, textiles or fleeces of synthetic polymides are preferably brightened optically with the compounds of the invention.

It is also possible to add the compounds of the invention to the materials to be brightened optically during their manufacturing processes or before their processing, for example to the viscose solution before spinning, or to the paper pulp. Suitable compounds may for example also be added to the spinning solution of polyamide-6 or polyamide-6,6 before processing, or to the low molecular weight starting materials before the polycondensation.

The compounds of the invention may also be used for optical brightening from anhydrous solvent systems, especially in the case where M in the formula I is hydrogen or an ammonium ion deriving from an organic nitrogen base.

Above all, the compounds of formula I in accordance with the present invention are distinguished by the fact that they give excellent degrees of whiteness on polyamide according to the exhaust processes and especially on cotton according to the pad-drying process, in crease-resistant finishing, according to the exhaust processes and under the conditions of washing. Thus, for example, high degrees of whiteness are obtained on polyamide according to the different exhaust processes in the usual temperature range of from 40° to 130° C.

The compounds of the invention are equally valuable when they are applied to cotton according to different processes. Thus, for example, excellent degrees of whiteness are obtained on cotton according to the pad-drying process.

The compounds of the invention may furthermore be applied in connection with synthetic resins and synthetic resin precondensates during the crease-resistant finishing of cellulose fibers and their blends with synthetic fibers according to the processes of dry and wet cross-linking ("wash and wear" finish of cellulose fibers). The cross-linking of the synthetic resins may be carried out in known manner in a large pH range of from 0 to 10. Thus, for example, especially the compounds of formula I in accordance with the present invention, where Z is the radical of a sulfo-aniline, especially the radical of 2,5-disulfo-aniline, are suitable for optically brightening cellulose materials from acidic cross-linking baths.

The liquors, at a content of up to 4 g of brightener per liter, are stable even at low pH of from 0 to 1 and give very good degrees of whiteness.

Above all, the compounds in accordance with the invention corresponding to formula I, where Z is an aniline radical, are distinguished as brighteners for cotton of high affinity, which, at small amounts, with or without the addition of electrolytes such as sodium sulfate, according to the exhaust process supply excellent degrees of whiteness with good color shade and high brilliancy.

The compounds of the invention are stable in bleaching baths to oxidative bleaching agents, for example hydrogen peroxide, and to reductive bleaching agents, for example sodium dithionite.

A further important application field for the compounds of the invention are detergents. Under gentle washing conditions, for example at 60° C, especially at low temperatures, for example at 30° C, very good brightening effects are obtained on cellulose fibers, on crease-resistant finished cellulose and on polyamide, as well as under boiling conditions on cellulose fibers, and there occurred no accumulation, that is, no greening, at amounts usual in practice (for example 0.05% by weight, relative to the detergent), also at repeated washings (for example 10 times).

The detergents used may contain known fillers and auxiliaries such as alkali metal silicates, alkali metal polyphosphates and -polymetaphosphates, alkali metal borates, alkali metal salts of carboxymethylcellulose, foam stabilizers such as alkanolamides of higher fatty acids or complexing agents such as soluble salts of ethylene-diamine-tetra-acetic acid or diethylene-triamine-penta-acetic acid, and chemical bleaching agents such as perborates or percarbonates.

Very good properties are also obtained when perborate containing detergents are used in the presence of perborate activators. Also the usual disinfectants employed in detergents do not have any influence on the brightening effect of the compounds of the invention.

Depending on the application and the desired effect, the amount of the compounds of the invention, relative to the material to be brightened optically, may vary within wide limits and is generally from about 0.01 to about 2% by weight.

The following examples illustrate the invention. The ratio of parts by weight to parts by volume is the same as that of kilogram to liter. Parts and percentages are by weight unless otherwise stated.

EXAMPLE 1

A solution of 18.44 parts of cyanuric acid chloride in 100 parts by volume of acetone are rapidly introduced with agitation into 400 parts of water having a temperature of 0° C. Subsequently, a solution of 18.52 parts of 4,4'-diaminostilbene-2,2'-disulfonic acid in 55 parts by volume of 2 N sodium hydroxide and 100 parts of water is added dropwise within 20 minutes at a temperature of from 0° to 5° C and at a pH of 2.5 to 3; the pH being maintained constant by simultaneously adding dropwise 2 N sodium carbonate solution. Agitation is continued for about one hour at a pH of 2.5 to 3 and a temperature of about 5° C, until no diamino-stilbene-disulfonic acid can be detected any more. Using a small amount of sodium carbonate solution, the pH is adjusted to 5, and a solution of 9.31 parts of aniline in 50 parts by volume of acetone is added dropwise within 15 minutes at 15° C; the pH being maintained at 5 to 5.5 by adding dropwise 2 N sodium carbonate solution. Subsequently, the whole is slowly heated to 40° C, and agitation is continued at this temperature for about 2 hours, while the pH is maintained constant until no aniline can be detected any more. Subsequently, the pH is adjusted to 7 by means of sodium carbonate solution, 20.42 parts by weight of 3-formylamino-propylamine (boiling point 105° – 106° C/3 torrs. $n_D^{25}$ 1.5200, mixture of 3-formylamino-propylamine and 1,4,5,6-tetrahydro-pyrimidine) are added, the whole is heated and aqueous acetone is distilled off, until a temperature of 100° C is attained. Subsequently, the mixture is refluxed for 6 hours, the pH being maintained at 8 to 9. After clarification with kieselguhr, the whole is cooled, salted out with sodium chloride, suction-filtered, washed to neutral with saturated sodium chloride solution, and dried. 31.38 parts of compound 5 (see Table), are obtained, calculated as 100% pure, having a residual moisture (determined according to Karl Fischer) and a sodium chloride content (determined by titration of the ionic chlorine).

EXAMPLE 2

Operations are carried out as described in Example 1, but in the second condensation step, a solution of 17.32 parts of metanilic acid in 60 parts by volume of 2 N sodium hydroxide and 100 parts of water are added dropwise instead of the solution of aniline in acetone. After salting out with sodium chloride, suction-filtration, washing to neutral with saturated sodium chloride solution and drying, 46.69 parts of the compound 6 (see Table), calculated as 100% pure, having a residual moisture and a sodium chloride content are obtained.

EXAMPLE 3

The first condensation step is carried out as described in Example 1. In the second condensation step, instead of aniline, a solution of 8.71 parts of morpholine in 50 parts by volume of acetone is added dropwise within 15 minutes at a temperature of from 10° to 20° C and a pH of from 5.5 to 6.5. Agitation is continued for another 3½ hours at room temperature; the cited pH being maintained constant by adding dropwise 2 N sodium carbonate solution. Subsequently, a pH of 7 is adjusted, 23.24 parts of 3-acetylamino-propylamine (boiling point 111° C/0.6 torr, $n_D^{25}$ 1.4819) are added, and operations are continued as indicated in Example 1. The condensation product is salted out with sodium chloride under heat and worked up as usual. 40.80 parts of compound 15 (see Table), calculated as 100% pure, are obtained.

EXAMPLE 4

The first and second condensation steps are carried out as indicated in Example 1. Subsequently, instead of 3-formylamino-propylamine, 23.24 parts of 3-acetylamino-propylamine are added, and the whole is worked up as indicated in Example 1. 33.10 parts of compound 16 (see Table), calculated as 100% pure, are obtained.

EXAMPLE 5

The first and second condensation step are carried out as indicated in Example 2. Subsequently, a pH of 7 is adjusted and, after addition of 23.24 parts of 3-acetylaminopropylamine, work-up is continued as indicated in Example 3. 45.60 parts of compound 19 (see Table), calculated as 100% pure, are obtained.

EXAMPLE 6

A solution of 18.44 parts of cyanuric acid chloride in 100 parts by volume of acetone are rapidly introduced into 400 parts of water having a temperature of 0° C. Subsequently, a solution of 25.33 parts of aniline-2,5-disulfonic acid in 70 parts by volume of 2 N sodium hydroxide and 100 parts of water is added dropwise within about one hour at a temperature of from 0° to 5°

C and a pH of 4; this pH being maintained constant by adding 2 N sodium carbonate solution. Agitation is continued for about 4 to 5 hours at 0° to 5° C and pH 4, until no aniline-2,5-disulfonic acid can be detected any more. The pH is subsequently adjusted to 7 by means of sodium carbonate solution, a solution of 18.52 parts of 4,4'-diamino-stilbene-2,2'-disulfonic acid in 55 parts by volume of 2 N sodium hydroxide and 100 parts of water is added dropwise within 10 minutes at pH 6.5 – 7, the whole is heated and agitation is continued for another 3 to 4 hours at 35° C and pH 6.5 – 7, until no diamino-stilene-disulfonic acid can be detected any more. The pH is maintained constant by adding dropwise 2 N sodium carbonate solution. Subsequently, 23.24 parts of 3-acetylamino-propylamine are added, agitation is continued again for one hour at 80° C, subsequently aqueous acetone is distilled off and agitation is continued again for 4 hours at 100° C and pH 8. The condensation product is salted out with sodium chloride while heating and worked up as usual. 55.30 parts of compound 20 (see Table), calculated as 100% pure, are obtained.

EXAMPLE 7

The first and the second condensation step are carried out as indicated in Example 1. Instead of 3-formylaminopropylamine, 26.04 parts of 1-methylamino-3-acetylaminopropane (boiling point 115° – 116° C/0.5 torr, $n_D^{25}$ 1.4741) are added at a pH of from 7 to 7.5. After having distilled off aqueous acetone, agitation is continued for 8 hours at 100° C, the pH not being allowed to drop below 8. Subsequently, the condensation product is clarified with kieselguhr, cooled, salted out with sodium chloride and worked up as usual. 26.40 parts of compound 24 (see Table), calculated as 100% pure, are obtained.

EXAMPLE 8

The first and the second condensation step are carried out as indicated in Example 6. In the third step, 26.04 parts of 1-methylamino-3-acetylamino-propane are added instead of 3-acetylamino-propylamine, and operations are continued as indicated in Example 7. The product is salted out with sodium chloride while heating and worked up as usual. 54.10 parts of compound 25 (see Table), calculated as 100% pure, are obtained.

EXAMPLE 9

The first and the second condensation step are carried out as indicated in Example 1. Subsequently, at a pH of 7, 45.66 parts of 3-tosylamino-propylamine (melting point 116° – 117° C) are added instead of 3-formylaminopropylamine, and operations are then continued as indicated in Example 1. The product is finally acidified with hydrochloric acid and suction-filtered after cooling, washed Congo neutral with water and dried. 47.10 parts of compound 31 (see Table), calculated as 100% pure, are obtained.

EXAMPLE 10

Operations are carried out as indicated in Example 9, but instead of 3-tosylamino-propylamine, 48.46 parts of 1-methylamino-3-tosylamino-propane (crude product from the hydrogenation of 3-tosylamino-propionitrile, melting point 82° – 83° C, in the presence of methylamine) are added. 37.60 parts of compound 32 (see Table), calculated as 100% pure, are obtained.

EXAMPLE of application 1

Exhaust process on cotton (using $Na_2SO_4$)

50 g samples of bleached cotton calico were treated with aqueous liquors at a goods-to-liquor ratio of 1.20, the liquors having the following composition:

0.25of one of the compounds 5, 6, 15, 16, 19, 20, 24, 25, 31 and 32, relative to the weight of the material, 5.0 g/l of Glauber's salt 2.0 g/l of a commercial textile softener of the fatty acidethanolamine ester type (fatty acid of mean chain length, about 16 carbon atoms)

The treatment was started at a temperature below 40° C; after immersion of the samples this temperature was raised to 60° C within 10 minutes, and the treatment was continued for a further 20 minutes at this temperature. The samples were subsequently dried without rinsing. The treatment yielded very good brightening effects of high brilliancy, especially in the case of the compounds 5, 6, 16, 19 and 24.

EXAMPLE of application 2

Exhaust process on cotton (without $Na_2SO_4$)

Material and operations were the same as described in Example of application 1, but there was no addition of Glauber's salt. Composition of the liquor:

0.25% of one of the compounds 5, 6, 16 and 24, relative to the weight of the samples, 2.0 g/l of a commercial textile softener of the fatty acidethanolamine ester type (fatty acid of mean chain length, about 16 carbon atoms)

Also this treatment yielded very good brightening effects of high brilliancy, especially when the compounds 5, 16 and 24 were used.

EXAMPLE of application 3

Pad-drying process on cotton 10 m each of cotton batiste (bleached) were padded on a foulard (padding mangle) with aqueous liquors. The liquors contained in each case:

1.2 g/l of one the compounds 5, 6, 15, 16, 19, 20, 24, 25, 31 and 32, 0.5 g/l of a commercial wetting agent on the basis of nonylphenol-polyglycol ether (9 ethyleneglycol units on the average), 10.0 g/l of a commercial textile softener on the basis of fatty acid-polyglycol ester (fatty acid of mean chain length, about 16 carbon atoms)

By squeezing-off between the foulard rollers, the liquor uptake was adjusted to about 70% of the dry weight of the samples. After the padding, the samples were dried on a stretching frame. The temperature of drying was 105° C. This treatment yielded very good and brilliant brightening effects, especially in the case of the componds 15, 16 and 24.

EXAMPLE of application 4

Dry cross-linking on cotton

Bleached poplin for shirts was impregnated on the laboratory foulard with aqueous liquors of the following composition:

180 g/l of dimethylolpropylene-urea,(1,3-dimethylolpyrimidone-2)

27 g/l of magnesium chloride-hexahydrate, 20 g/l of a commercial textile softener (basis trimethylolalkyl-urea with $C_{16}/C_{18}$- alkyl)

30 g/l of a usual additive (basis polyethylene dispersion)

2 g/l of nonylphenol-oxyethylate (9 ethyleneglycol units on the average)

2 g/l of one of the compounds 5, 6, 15, 16, 19, 20, 24, 25, 31 and 32.

The single samples were squeezed off to achieve a liquor uptake of about 70% of the dry weight, and subsequently dried on a stretching frame at 105° C.

Subsequently, condensation was carried out at 155° C for 3 minutes. Especially the compounds 6, 15, 16, 19, 20 and 25 yielded very good brightening effects of high brilliancy.

EXAMPLE of application 5

Wet cross-linking on cotton

Samples of 10 m each of cotton damask were padded on a foulard with aqueous liquors having the following compositions:

300 g/l of dimethylol-dihydroxy-ethylene-urea (1.3-dimethylol-4,5-dihydroxy-imidazolone-2)

100 ml/l of hydrochloric acid, about 36% strength 2 g/l of nonylphenol-oxethylate (9 ethylene glycol units on the average)

2.0 g/l of one of the compounds 5, 6, 19, 20 and 25.

After having squeezed off to about 70% of liquor uptake (relative to the dry weight) the samples were wound up without tension and, tightly wrapped in polyethylene sheets and stored for 20 hours at room temperature. Afer this time, the samples were washed with baths of the following compositions:

1th bath: cold water

2nd bath: cold water and 10 g/l of sodium carbonate, calcined

3rd bath: water having a temperature of 40° – 60° C, + 1 g/l of nonylphenol-oxethylate (9 ethyleneglycol units on the average) + 2 g/l of sodium carbonate, calcined 4th bath: water having a temperature of 40° to 50° C.

After having well squeezed off, the samples were subsequently finished wet-in-wet wih 50 g/l of a commercial textile softener on the basis of trimethylolalkyl-urea ($C_{16}/C_{18}$ alkyl) and dried on a stretching frame at 100° C. This treatment yielded very good brightening effects, especially when the compounds 20 and 25 were used.

EXAMPLE of application 6

Peroxide bleaching and brightening of cotton

Samples of cotton interlock were treated in aqueous liquors of the following composition:

2.5 ml/l of hydrogen peroxide solution (about 35% strength)

1.0 ml/l of a stabilizer on the basis of sodium salt of a polycarboxylic acid 1.0 g/l of a commercial wetting agent on the basis of epoxylated phenylsulfonic acid-Na ($C_{12}/C_{14}$ alkyl) and tributylphenol-polyglycol ether (8 ethylene glycol units on the average)

1.5 g/l of sodium hydroxide 5.0 g/l of Glauber's salt 0.25% of one of the compounds 5, 6, 15, 16, 19, 20, 24, 25, 31 and 32, relative to the weight of the samples. The goods-to-liquor ratio was 1:2.

The samples were introduced into the baths at a temperature below 40° C, the temperature of the liquor was then raised to 80° – 85° C within 30 minutes, and treatment was continued at this temperature for a further 60 minutes. Rinsing and drying were carried out as usual. In this manner, good brightening effects of reddish-violet fluorescence were obtained especially in the case of the compounds 5, 6, 16, 19 and 24.

EXAMPLE of application 7

Exhaust process of viscose staple fiber fabric (with $Na_2SO_4$)

At a goods-to-liquor ratio of 1:20, samples of viscose staple fiber fabrics were treated according to the exhaust process with aqueous liquors having the following composition:

0.25% of one of the compounds 5, 6, 15, 16, 19, 20, 24 and 25, each relative to the weight of the samples 5.0 g/l of Glauber's salt.

The samples of fabric were introduced into liquor at about 40° C. Within about 10 minutes, the liquor temperature was raised to 60° C, and the samples were treated at this temperature for a further 30 minutes. They were then rinsed and dried as usual. A very good brightening effect was obtained, especially in the case of the compounds 5, 16 and 24.

EXAMPLE of application 8

Exhaust process on viscose staple fiber fabric (without $Na_2SO_4$)

Material and operations were the same as described in Example of application 7, but there was no addition of Glauber's salt. The liquors thus contained only 0.25% of one of the compounds 5, 6, 15, 16 and 24, relative to the weight of the samples. These compounds yielded very good brightening effects also without addition of the salt, especially the compounds 5, 16 and 24.

EXAMPLE of application 9

Fine laundering of polyamide-6

Samples of knitted fabrics of polycaprolactam were subjected to repeated fine laundering in a household washing machine. They were washed 10 times at a goods-to-liquor ratio of 1:2 in each case. Each washing cycle took 15 minutes, the washing temperature was 60° C. The detergent concentration of the liquors was 5 g/l; the light-duty detergent having the following composition:

10% of isotridecanol-polyglycol ether (8 ethyleneglycol units on the average)

50% of sodium tripolyphosphate

6% of sodium metasilicate

4% of carboxy-methylcellulose (salt containing, about 60% strength, viscosity 1500 cP at 20° C in a 5% solution, normally etherified)

1% of fatty alcohol $C_{16}/C_{18}$

29% of sodium sulfate 0.05% of one of the compounds 5, 6, 15, 16, 19, 24, 25 and 32, (the amount of brightener being relative to the detergent mixture). After the 10 washings, the knitted fabrics were very well brightened without any accumulations showing.

EXAPLE of application 10

Fine laundering of crease-resistant finished cotton a. at 60° C

Samples of crease-resistant finished cotton poplin for shirts (finish with dimethylol-dihydroxy-ethylene-urea according to the dry cross-linking process) were washed as indicated in Example of application 9. The following optical brighteners were added to the light-duty detergent formulation specified there:
0.05% each of one of the compounds 5, 6, 16, 24 and 25, relative to the detergent mixture. Excellent brightening effects were obtained, especially in the case of the compounds 5, 6, 16 and 24, and no accumulations were observed.

b. at 30° C

Samples of crease-resistant finished cotton poplin for shirts (finish as indicated above) were washed as indicated in Example of application 9, but at a temperature of only 30° C. 0.05% each of the compounds 16 and 24, relative to the detergent mixture, were added to the above-mentioned detergent formulation. Very good brightening effects were obtained in both cases.

EXAMPLE of application 11

Washing of cotton at boiling temperature

Bleached cotton calico was subjected to 10 washings at boiling temperature. At a goods-to-liquor ratio of 1:20 and a liquor temperature of 98° C, the time of washing was 15 minutes in each case. 5 g/l of a heavy-duty detergent having the following composition were used:

12% of nonylphenol-polyglycol ether (10 ethyleneglycol units on the average)
40% of sodium tripolyphosphate
10% of sodium metasilicate
3% of carboxymethylcellulose (same type as in Example of application 9)
1% of fatty alcohol $C_{16}/C_{18}$
34% of sodium sulfate
0.05% of one of the compounds 5, 6, 16 and 24, relative to the detergent mixture. Excellent brightening effects were obtained. No accumulations were observed after 10 washings.

EXAMPLE of application 12

Washing of crease-resistant finished cotton at boiling temperature

Samples of crease-resistant finished cotton poplin for shirts (dry cross-linking with dimethylol-dihydroxy-ethylene-urea) were treated according to Example of application 11. Also the optical brighteners used were the same as indicated in the above Example.

Also in this case, excellent degrees of whiteness without accumulations were obtained, especially in the case of compounds 5, 16 and 24.

EXAMPLE of application 13

Exhaust process on polyamide-6 50 kg each of polyamide-6 knitted fabric were treated in a winch vat according to the exhaust process at a goods-to-liquor ratio of 1:20 with liquors having the following composition:

0.25% of one of the compounds 5, 6, 15, 16, 19, 24, 25, 31 and 32, relative to the weight of the samples,
0.5 g/l of nonylphenol-polyglycol ether (10 ethyleneglycol units on the average)
Operations were carried out at a pH of the aqueous liquor of 4.0, adjusted by means of oxalic acid, and a temperature of 80° C. The time of treatment was 30 minutes. Rinsing and drying were carried out as usual. This method yielded very good brightening effects, especially in the case of the compounds 5, 15, 16, 24, 31 and 32.

EXAMPLE of application 14

High temperature process on polyamide-6,6

20 kg each of polyamide-6,6 knitted fabric were brightened optically in a beam dyeing apparatus under the following conditions:
goods-to-liquor ratio: 1:20
0.5 g/l of nonylphenol-polyglycol ether (10 ethyleneglycol units on the average)
2.0 g/l of reductive bleaching agent on the basis of sodium dithionite
0.25% of one of the compounds 5, 6, 15, 16, 19, 20, 24, 31 and 32, relative to the weight of the samples. Starting at a temperature of about 40° C, the temperature was raised to 120° C within 15 minutes, and the treatment was continued at this temperature for 45 minutes. The samples were then finished as usual. This method yielded good brightening effects on the polyamide-6,6 samples, especially in the case of compounds 6 and 24.

EXAMPLE of application 15

Exhaust process on polyurethane 5 m each of knitted fabric made from polyurethane elastomeric filaments were prewashed at 80° C with
2 g/l of nonylphenol-glycol ether (10 ethyleneglycol units on the average)
2 g/l of condensed phosphate,
the goods-to-liquor ratio being 1:30, the time of washing 30 minutes. Subsequently, the samples were brightened in liquors having the following composition:
goods-to-liquor ratio 1:20
0.5 g/l of nonylphenol-polyglycol ether (10 ethyleneglycol units on the average)
2.0 g/l of reductive bleaching agent on the basis of sodium dithionite
0.25% of one of the compounds 5, 6, 15, 16, 19, 20 and 25, relative to the weight of the samples.
Formic acid to adjust pH 4.0
The samples were introduced into the liquor at about 40° C, and the temperature was then raised within 10 minutes to 80°C. The treatment of the material was continued at this temperature for a further 20 minutes. Rinsing and drying were carried out as usual.

Very good brightening effects were obtained, especially in the case of compound 19.

EXAMPLE of application 16

Exhaust process on wool

Samples of wool gabardine were prewashed in the following liquor: goods-to-liquor ratio: 1:30
1 g/l of isotridecanol-polyglycol ether (8 ethyleneglycol units on the average)
0.5 ml/l of ammonia (25%)
Washing time: 30 minutes, washing temperature: 40° – 50° C. Subsequently, the samples were bleached as follows: goods-to-liquor ratio 1:40
20 ml/l of hydrogen peroxide (about 35% strength)
1.5 g/l of tetrasodium pyrophosphate, crystallized ammonia (of 25% strength) to adjust pH 9.5
Bleaching was carried out for 4 hours at a temperature of 40° – 50° C, subsequently, the samples were rinsed in warm and cold water. The samples of fabric so bleached were brightened with liquors of the following composition: goods-to-liquor ratio 1:20

2 g/l of reductive bleaching agent on the basis of sodium dithionite, 0.15% of one of the compounds 5, 16 and 24, relative to the weight of the samples. The samples were treated in this liquor for 1 hour at 50°C, the liquor was then adjusted to pH 4 by means of oxalic acid, and the treatment was continued at 60°C for a further 30 minutes. Rinsing and drying were carried out as usual. As compared to the starting material, pronounced brightening effects were obtained.

| No. | Z | $R_1$ | A | NXY | M | λ Abs. max. [mμ] | $10^{-4}$ |
|---|---|---|---|---|---|---|---|
| 1 | $C_6H_5$—NH— | H | $(CH_2)_2$ | —NH—CO—$CH_3$ | H | 353 | 4.77 |
| 2 | " | " | " | " | $HN(CH_2$—$CH_2$—$OH)_3$ | 354 | 4.81 |
| 3 | " | " | " | " | $HN(C_2H_5)_3$ | 354 | 5.31 |
| 4 | " | " | —CH—$CH_2$— <br> \| <br> $CH_3$ | " | H | 353 | 5.04 |
| 5 | " | " | $(CH_2)_3$ | —NH—CO—H | Na | 355 | 6.27 |
| 6 |  | " | " | " | " | 356 | 6.34 |
| 7 | Cl | " | " | —NH—CO—$CH_3$ | " | 354 | 5.60 |
| 8 | $H_3C$—NH— | " | " | " | " | 353 | 5.72 |
| 9 | $H_3C$—CO—NH—$(CH_2)_3$—NH— | " | " | " | " | 353 | 4.60 |
| 10 | $H_3C$—$(CH_2)_{17}$—NH— | " | " | " | " | 356 | 6.18 |
| 11 | $H_2C$=CH—$CH_2$—NH— | " | " | " | " | 353 | 5.45 |
| 12 | $NaO_3S$—$(CH_2)_2$—N— <br> \| <br> $CH_3$ | " | " | " | Na | 353 | 4.83 |
| 13 | (HO—$CH_2$—$CH_2$)$_2$N— | " | " | " | " | 354 | 5.21 |
| 14 |  | " | " | " | " | 356 | 6.17 |
| 15 |  | " | " | " | " | 356 | 5.95 |
| 16 | $C_6H_5NH$ | " | " | " | " | 354 | 5.96 |
| 17 | " | " | " | " | H | 353 | 5.28 |
| 18 | " | " | " | " | $H_2N(CH_2$–$CH_2$–$OH)_2$ | 354 | 5.50 |
| 19 |  | " | " | " | Na | 353 | 6.28 |
| 20 | 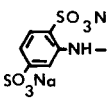 | " | " | " | " | 357 | 6.43 |
| 21 | $H_3C$—O— | " | " | " | " | 354 | 5.91 |
| 22 | $H_3C$—O—$CH_2$—$CH_2$—O— | " | " | " | " | 353 | 4.79 |
| 23 | $C_6H_5$—O— | " | " | " | H | 353 | 5.08 |
| 24 | $C_6H_5NH$ | —$CH_3$ | " | " | Na | 356 | 6.14 |
| 25 |  | " | " | " | " | 357 | 6.60 |
| 26 | $C_6H_5NH$— | $H_3C$-CO-N-H-$(CH_2)_3$ | " | " | H | 353 | 4.82 |
| 27 | " | H | " | NH—CO—$(CH_2)_{16}$—$CH_3$ | Na | 355 | 4.90 |
| 28 | " | " | " | —NA—CO—$C_6H_5$ | " | 353 | 5.21 |
| 29 | " | " | " | —NH—CO—O—$C_2H_5$ | " | 353 | 5.40 |
| 30 | " | " | " | —NH—CO—NH—$C_6H_5$ | " | 355 | 4.87 |
| 31 | " | " | " | —NH-$SO_2$--$CH_3$ | H | 360 | 5.25 |
| 32 | " | —$CH_3$ | " | " | " | 360 | 4.36 |
| 33 | " | H | " | —N$\begin{array}{l}CO—CH_3\\CH_3\end{array}$ | " | 357 | 4.18 |

-continued

| No. | Z | R₁ | A | NXY | M | λ Abs. max. [mμ] | 10⁻⁴ |
|---|---|---|---|---|---|---|---|
| 34 | " | " | " | -N(CO-CH₃)(H) (cyclohexyl) | " | 351 | 5.17 |
| 35 | " | " | " | -N(CO-CH₃)(C₆H₅) | " | 353 | 4.70 |
| 36 | " | " | " | -N(CO-CH₂)(CO-CH₂) | Na | 354 | 5.20 |
| 37 | C₆H₅NH— | " | " | -NH-CO-CH₂-CH₂-CO₂Na | Na | 353 | 4.71 |
| 38 | O(N)— (morpholino) | " | " | -N(CH₂-CH₂-CH₂)(CO-CH₂-CH₂) | H | 355 | 6.10 |
| 39 | C₆H₅NH— | " | " | -N(CO)(CO)-phthalimido | Na | 355 | 5.81 |
| 40 | 2,4-(SO₃Na)₂C₆H₃-NH— | " | " | " | " | 352 | 5.41 |
| 41 | C₆H₅—NH— | " | " | -N-pyridone | Na | 353 | 5.26 |
| 42 | 2,4-(SO₃Na)₂C₆H₃-NH— | " | " | " | " | 354 | 4.87 |
| 43 | C₆H₅—NH— | " | " | (CH₂)₄ | -NH-CO-NH₂ | " | 355 | 5.40 |
| 44 | " | " | " | (CH₂)₅ | -NH-CO-CH₃ | " | 353 | 5.18 |
| 45 | " | " | " | (CH₂)₆ | -NH-SO₂-C₆H₅ | Na | 358 | 4.50 |

We claim:
1. A compound of the formula

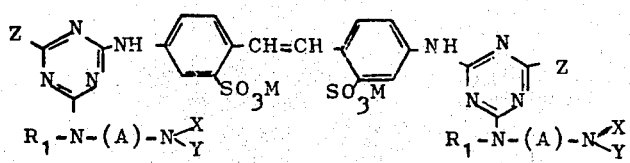

in which
X is —CO—R₂, —SO₂—R₃, CO—O—R₃, —CO—NH—R₂ or —CS—NH—R₂,
Y is —CO—R₃ or R₄, or, if X is —CO—R₂,
Y and R₂ together form a chain of 3 to 5 carbon atoms which chain consists of the following ring members:
  a groups of the formula —CH₂—,
  b groups of the formula —CH=CH—,
  c groups of the formula

and
  d groups of the formula -CO-, wherein a is an integer of zero to 5,
b is an integer of zero to 2 and
c and d are zero or 1, with the proviso that a is more than 3 if b, c and d all are zero,
R₁, R₂ and R₄ are hydrogen, alkyl of 1 to 20 carbon atoms, cycloalkyl of 4 to 8 carbon atoms or phenyl,
R₃ is alkyl or 1 to 20 carbon atoms, cycloalkyl of 4 to 8 carbon atoms or phenyl,
A is alkylene of 2 to 6 carbon atoms,
Z is chlorine or a group of the formula —NR₅R₆ or —O—R₇, wherein
R₅ is hydrogen, alkyl or alkenyl of up to 20 carbon atoms, cycloalkyl of 4 to 8 carbon atoms or phenyl,
R₆ is hydrogen or lower alkyl, or $R_5$ and $R_6$ together with the nitrogen to which they are bound are pyrrolidino, piperidino, hexamethyleneimino or morpholino, $R_7$ is lower alkyl or phenyl and M is hydrogen or a colorless cation, which groups $R_1$, $R_2$, $R_3$, $R_4$, $R_5$, $R_6$ and $R_7$ are unsubstituted or substituted by non-chromophoric radicals selected from the group consisting of lower alkyl, lower alkenyl, lower alkoxy, lower alkanoyl, benzoyl, halogen, amino, lower alkylamino, di-lower-alkyl-amino, tri-lower-alkylammonium, hydroxy, lower alkanoyloxy, benzoyloxy, lower alkanoylamino, benzoylamino, carboxy, lower carboalkoxy, carbamoyl, mono- and di-N-(lower alkyl) carbamoyl, cyano, sulfo, sulfonic acid lower alkyl ester, sulfonic acid amide, sulfonic acid mono- and di-N-(lower alkyl) amide and phenyl.

2. A compound as defined in claim 1, wherein $R_1$ is hydrogen, lower alkyl, cyclohexyl or lower alkyl substituted by hydroxy, lower alkoxy or -NXY wherein X and Y is defined as below, X is —CO—$R_2$, —CO—NH—$R_2$, —$SO_2$—$R_3$ or —CO—O—$R_3$, wherein $R_2$ is hydrogen; alkyl of 1 to 18 carbon atoms; lower hydroxyalkyl, lower carboxyalkyl, lower sulfoalkyl, lower phenylalkyl, cyclohexyl, phenyl, chlorophenyl, lower alkylphenyl or lower alkoxyphenyl, $R_3$ is lower alkyl, benzyl, phenyl, tolyl, Y is hydrogen, lower alkyl, cyclohexyl or phenyl or, if X is —CO—$R_2$, $R_2$ and Y together are alkylene of 4 or 5 carbon atoms, alkyleneoxo having 2 to 4 carbon atoms in the alkylene moiety, ethyleneoxo, ortho-phenyleneoxo or butadienylene.

A is alkylene of 2 to 6 carbon atoms,

Z is chlorine or a group of the formula —$NR_5R_6$ or —O—$R_7$ wherein $R_5$ is hydrogen; lower alkyl which is unsubstituted or substituted by hydroxy, lower alkoxy, carboxy, sulfo or phenyl; lower alkenyl; cyclohexyl; phenyl which is unsubstituted or substituted by chlorine, lower alkyl, lower alkoxy, carboxy or sulfo; or a group of the formula —A—NXY in which A, X and Y are defined as above, $R_6$ is hydrogen, lower alkyl or lower alkyl substituted by hydroxy, carboxy, sulfo or lower alkoxy, or $R_5$ and $R_6$ together with the nitrogen to which they are bound are pyrrolidino, piperidino, hexamethyleneimino or morpholino, $R_7$ is lower alkyl, phenyl or lower alkyl substituted by lower alkoxy, and M is hydrogen, alkali metal, one equivalent of an alkaline earth metal or an ammonium ion of the formula —$H_xNR_{4-x}$ in which $x$ is 1 to 4 and R is lower alkyl or lower hydroxyalkyl.

3. A compound as defined in claim 1, wherein $R_1$ is hydrogen, lower alkyl or —A—NXY in which A, X and Y are defined as below, X is —CO—$R_2'$, —CO—NH—$R''_2$, —$SO_2$—$R'_3$ or —CO—O—$R''_3$, wherein $R'_2$ is hydrogen, alkyl of 1 to 18 carbon atoms, lower carboxyalkyl or phenyl, $R''_2$ is hydrogen, lower alkyl or phenyl, $R'_3$ is phenyl or tolyl, $R''_3$ is lower alkyl or phenyl Y is hydrogen or, if $R'_2$ is lower alkyl, Y is also lower alkyl, cyclohexyl or phenyl or Y and $R'_2$ together are alkylene of 4 or 5 carbon atoms, ethyleneoxo, orthophenyleneoxo or butadienylene, A is alkylene of 2 to 6 carbon atoms, Z is chlorine or a group of the formula —$NR_5R_6$ or —O—$R_7$, wherein $R_5$ is alkyl of 1 to 18 carbon atoms, lower alkenyl, phenyl, sulfophenyl, lower alkyl substituted by hydroxy, carboxy or sulfo, or $R_5$ is —A—NXY in which A, X and Y are as defined above, $R_6$ is hydrogen, lower alkyl or lower hydroxyalkyl or $R_5$ and $R_6$ together with the nitrogen to which they are bound are pyrrolidino, piperidino or morpholino, $R_7$ is lower alkyl, phenyl or lower alkyl substituted by lower alkoxy, and M is hydrogen, alkali metal or an ammonium group of the formula $H_xNR_{4-x}$ in which x is 1 to 4 and R is lower alkyl or hydroxyethyl.

4. A compound as defined in claim 1, wherein

X is —$COR_2$, $R_2$ being hydrogen or methyl,

Y is hydrogen, $R_1$ is hydrogen or methyl,

Z is —$NR_5R_6$, $R_5$ being phenyl or mono- or disulfophenyl and $R_6$ being hydrogen or $R_5$ and $R_6$ together with the nitrogen are morpholino, A is ethylene or propylene and M is hydrogen, alkali metal or a group of the formula $H_xNR_{4-x}$, in which x is 1 to 4 and R is methyl, ethyl or hydroxyethyl.

5. A compound as defined in claim 1, wherein

X is formyl or acetyl,

Y is hydrogen, $R_1$ is hydrogen or methyl,

Z is anilino or mono- or disulfoanilino,

A is ethylene or propylene and

M is hydrogen, sodium, potassium or $H_xNR_{4-x}$ wherein x is 1 to 4 and R is methyl, ethyl or hydroxyethyl.

6. The compound as defined in claim 1, wherein X is acetyl, Y and $R_1$ are hydrogen, A is propylene, Z is anilino and M is sodium.

7. The compound as defined in claim 1, wherein X is acetyl, Y is hydrogen, $R_1$ is methyl, Z is anilino, A is propylene and M is sodium.

8. The compound as defined in claim 1, wherein X is acetyl, $R_1$ and Y are hydrogen, A is ethylene, Z is anilino and M is hydrogen.

9. The compound as defined in claim 1, wherein X is formyl, Y and $R_1$ are hydrogen, Z is propylene, Z is anilino and M is sodium.

10. The compound as defined in claim 1, wherein X is formyl, Y and $R_1$ are hydrogen, A is propylene, Z is sulfoanilino sodium salt and M is sodium.

11. The compound as defined in claim 1, wherein X is acetyl, Y and $R_1$ are hydrogen, A is propylene, Z is disulfoanilino sodium salt and M is sodium.

12. The compound as defined in claim 1, wherein X is acetyl, Y and $R_1$ are hydrogen, A is propylene, Z is morpholino and M is sodium.

* * * * *